United States Patent
Milner et al.

(10) Patent No.: US 9,877,742 B2
(45) Date of Patent: Jan. 30, 2018

(54) THROMBECTOMY CATHETER WITH FLOW DIRECTING MECHANISM

(71) Applicant: Cook Medical Technologies LLC, Bloomington, IN (US)

(72) Inventors: Keith Milner, West Lafayette, IN (US); Angela Barnett, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 574 days.

(21) Appl. No.: 14/453,921

(22) Filed: Aug. 7, 2014

(65) Prior Publication Data

US 2015/0133973 A1  May 14, 2015

Related U.S. Application Data

(60) Provisional application No. 61/904,178, filed on Nov. 14, 2013.

(51) Int. Cl.
*A61B 17/3207* (2006.01)
*A61B 17/22* (2006.01)
*A61B 17/3203* (2006.01)

(52) U.S. Cl.
CPC .......... *A61B 17/3207* (2013.01); *A61B 17/22* (2013.01); *A61B 17/32037* (2013.01); *A61B 2017/22001* (2013.01); *A61B 2017/22065* (2013.01); *A61B 2017/22079* (2013.01); *A61B 2017/22084* (2013.01); *A61B 2017/22094* (2013.01); *A61B 2217/007* (2013.01)

(58) Field of Classification Search
CPC ........ A61B 17/3207; A61B 17/320716; A61B 2017/320733; A61B 17/22; A61B 2017/22001; A61B 17/22012; A61B 2217/005; A61B 2217/007; A61B 2017/22079; A61B 2017/22082; A61B 2017/22081; A61B 2017/22084; A61B 17/32037
See application file for complete search history.

(56) References Cited

U.S. PATENT DOCUMENTS

| | | | |
|---|---|---|---|
| 4,762,130 A * | 8/1988 | Fogarty | A61B 17/22032 604/103.07 |
| 5,135,484 A * | 8/1992 | Wright | A61B 17/22 604/101.03 |
| 5,601,537 A | 2/1997 | Frassica | |
| 6,063,069 A | 5/2000 | Cragg et al. | |
| 6,379,334 B1 | 4/2002 | Frassica | |
| 8,398,579 B2 | 3/2013 | Morris et al. | |
| 8,439,878 B2 | 5/2013 | Bonnette et al. | |
| 2003/0055445 A1 | 3/2003 | Evans et al. | |

(Continued)

*Primary Examiner* — Tuan V Nguyen
*Assistant Examiner* — Chima Igboko
(74) *Attorney, Agent, or Firm* — Liell & McNeil

(57) ABSTRACT

A thrombectomy catheter includes a catheter body having first and second lumens formed therein, and a flow directing mechanism upon a distal body end forming a channel for conveying fluid between an outlet and an inlet fluidly connected with the first and second lumens. The channel axially and circumferentially advances about the catheter body, and is positioned between the outlet and inlet such that fluid conveyed by the channel enters a suction stream flowing to the inlet and entraining material of disrupted thrombus.

13 Claims, 3 Drawing Sheets

(56) References Cited

U.S. PATENT DOCUMENTS

| | | | |
|---|---|---|---|
| 2005/0228417 A1* | 10/2005 | Teitelbaum | A61B 17/22031 606/159 |
| 2008/0167678 A1* | 7/2008 | Morsi | A61B 17/32072 606/200 |
| 2011/0112562 A1 | 5/2011 | Torrance | |
| 2012/0116438 A1 | 5/2012 | Salahieh et al. | |
| 2013/0072756 A1 | 3/2013 | Frassica et al. | |
| 2013/0103063 A1 | 4/2013 | Escudero et al. | |

* cited by examiner

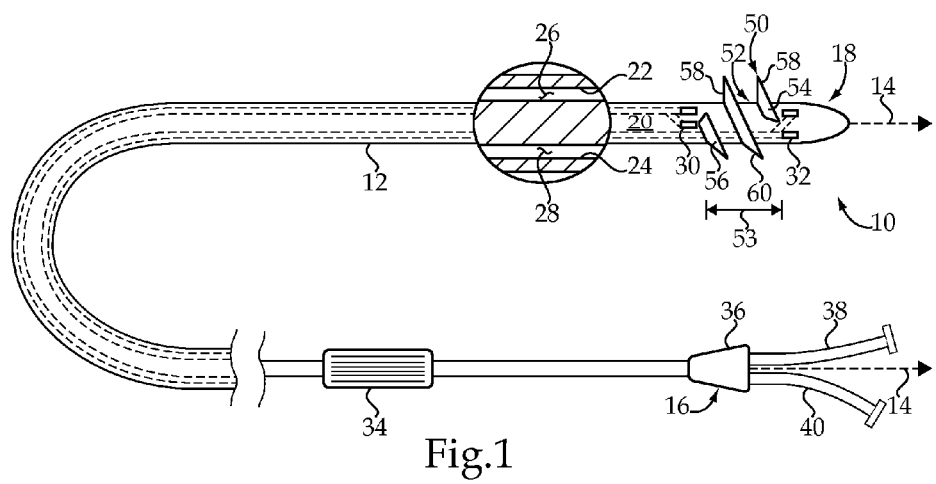
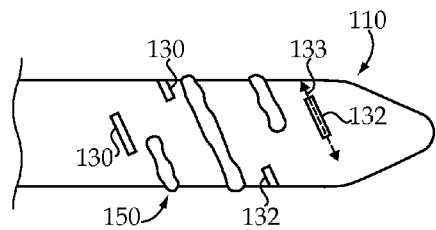
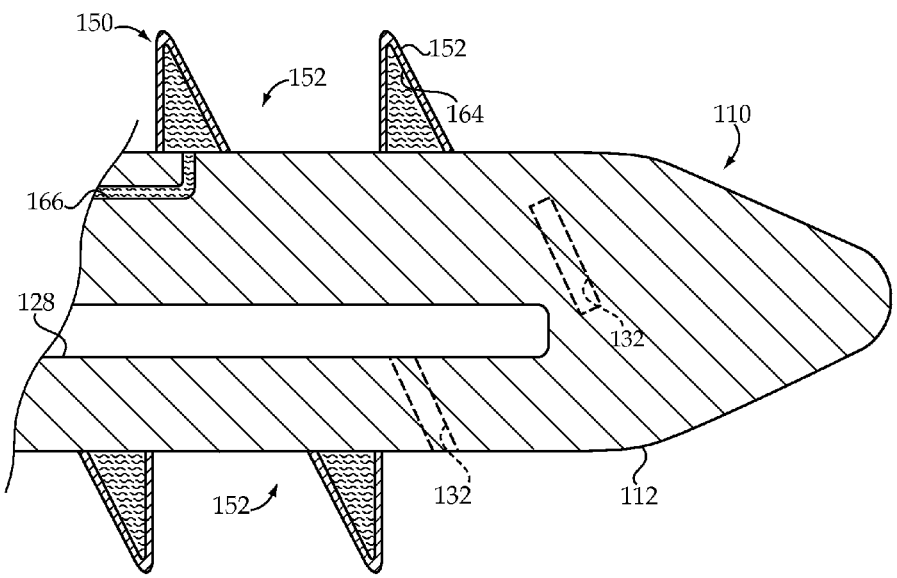
Fig.1
Fig.2
Fig.3

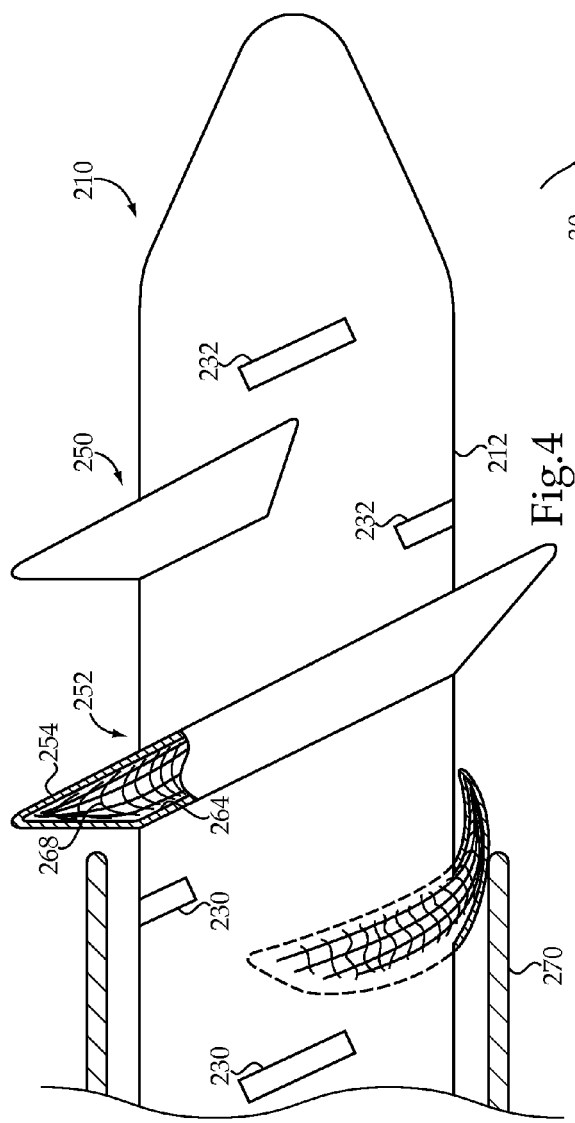
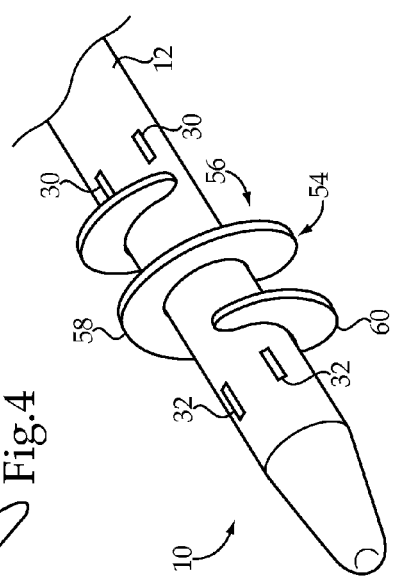

THROMBECTOMY CATHETER WITH FLOW DIRECTING MECHANISM

TECHNICAL FIELD

The present disclosure relates generally to devices and methodology for disrupting thrombus, and more particularly to directing fluid between an outlet and an inlet via an axially and circumferentially advancing channel in a thrombectomy catheter.

BACKGROUND

A variety of techniques are used to treat blood clots in patients. Infusion is commonly used to deliver a thrombolytic agent into a blood vessel in a patient, such as a vein, for dissolving the material of the blood clot or thrombus. Other techniques utilize mechanical action of a percutaneously introduced tool to break up thrombus material, for removal from the patient. Specially designed catheters with augers or various other cutting implements, sometimes used in combination with thrombolytics, are well known and widely used.

Rheolytic thrombectomy is yet another technique used to treat blood clots, and exploits the creation of a vacuum by high velocity fluid injected into and withdrawn from a body lumen in a patient to both disrupt a thrombus and draw its fragments out of the vessel. Increased fluid velocity near ports in a rheolytic catheter leads to reduced pressure creating the vacuum according to well known fluid dynamic principles. One standard design for a rheolytic thrombectomy catheter is sold under the trade name Angiojet®. Another rheolytic thrombectomy catheter is known from U.S. Pat. No. 8,439,878 B2 to Bonnette et al. The catheter in Bonnette et al. has a self-inflating balloon with drug infusion capabilities, where the self-inflation apparently occurs in response to flow of fluid from a fluid jet emanator to inflow orifices located distal to the balloon. While these and other rheolytic thrombectomy catheters are in widespread use, there is always room for improvement.

SUMMARY OF THE DISCLOSURE

In one aspect, a thrombectomy catheter includes an elongate catheter body defining a longitudinal axis extending between a proximal body end and a distal body end, and including an outer surface, and inner surfaces defining a longitudinally extending first lumen and a longitudinally extending second lumen. The first lumen is fluidly connected with an outlet formed in the outer surface and located in the distal body end, and the second lumen is fluidly connected with an inlet formed in the outer surface and located in the distal body end for receiving fluid pumped from the outlet to the inlet for suction disruption of the thrombus. The catheter further includes a flow directing mechanism upon the distal body end forming a channel for conveying a portion of the fluid. The channel axially and circumferentially advances about the elongate catheter body, and is positioned between the outlet and inlet such that fluid having exited the channel enters a suction stream flowing to the inlet and entraining material of the disrupted thrombus.

In another aspect, a method of treating thrombus in a patient includes pumping fluid between an outlet and an inlet in a thrombectomy catheter defining a longitudinal axis and positioned within a body lumen in a patient. The method further includes disrupting a thrombus within the body lumen via suction induced by a lowered pressure of the pumped fluid flowing between the outlet and the inlet. The method further includes conveying a portion of the pumped fluid through an axially and circumferentially advancing channel formed by the thrombectomy catheter between the outlet and the inlet, such that fluid having exited the channel enters a suction stream flowing to the inlet and entraining material of the disrupted thrombus.

BRIEF DESCRIPTION OF THE DRAWINGS

FIG. 1 is a partially sectioned side diagrammatic view of a catheter, according to one embodiment;

FIG. 2 is a side diagrammatic view of a portion of a catheter in a first state, according to one embodiment;

FIG. 3 is a sectioned side diagrammatic view of the catheter portion of FIG. 2, in a second state;

FIG. 4 is a partially sectioned side diagrammatic view of a catheter, in multiple section planes, according to another embodiment;

FIG. 5 is a partial perspective view of the catheter of FIG. 1; and

DETAILED DESCRIPTION

Figure 6:
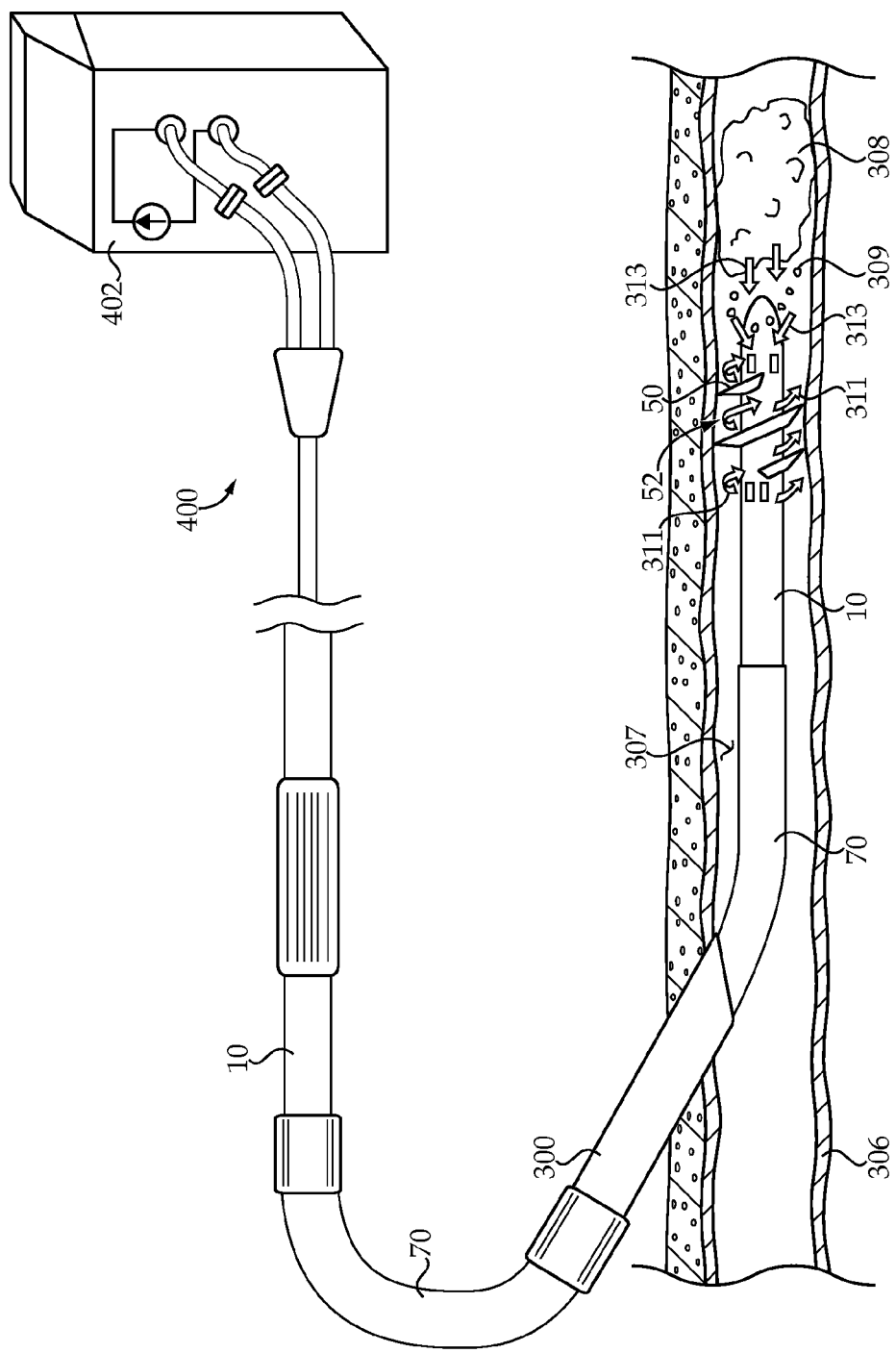
FIG. 6 is a side diagrammatic view of a catheter in a thrombectomy system, at one stage of a treatment procedure.

Referring to FIG. 1, there is shown a thrombectomy catheter 10 according to one embodiment. Catheter 10 includes an elongate catheter body 12 defining a longitudinal axis 14 extending between a proximal body end 16 and a distal body end 18. Catheter body 12 includes an outer surface 20, a first inner surface 22 defining a longitudinally extending first lumen 26, and a second inner surface 24 defining a longitudinally extending second lumen 28. A manifold 36 is located at proximal body end 16, and connects with a leader tube 40 fluidly connecting with first lumen 26, and another leader tube 38 fluidly connecting with second lumen 28. A handle 34 is coupled with catheter body 12 to enable a clinician to manipulate catheter 10 within a body lumen in a patient.

First lumen 26 is fluidly connected with an outlet 30 formed in outer surface 20, and will typically be fluidly connected with a plurality of outlets 30 spaced circumferentially and potentially axially about catheter body 12. The one or more outlets 30 are formed in distal body end 18. Second lumen 28 is fluidly connected with an inlet 32, typically a plurality of inlets, formed in outer surface 20 and located in distal body end 18 for receiving fluid pumped from outlet 30 to inlet 32 for suction disruption of a thrombus, as further discussed herein. Descriptions in the present disclosure of "outlet" or "inlet" in the singular should be taken to analogously refer to multiple outlets or inlets, except where otherwise indicated. As will be further apparent from the following description, catheter 10 is uniquely configured for conveyance of fluid pumped from outlet 30 to inlet 32 during thrombectomy procedures so as to optimize the suction attained for a given volumetric flow rate.

To this end, catheter 10 further includes a flow directing mechanism 50 upon distal body end 18 forming a channel 52 for conveying a portion of the pumped fluid. Channel 52 axially and circumferentially advances about catheter body 12, and is positioned between outlet 30 and inlet 32 such that fluid having exited channel 52 enters a suction stream flowing to inlet 32 and entraining material of a disrupted thrombus. Those skilled in the art will be familiar with thrombectomy catheters which exploit the fluid dynamic properties of fluid flowing from an outlet to an inlet in a thrombectomy catheter to create a lowered pressure fluid stream that induces suction within a body lumen to break apart a thrombus and evacuate material of the thrombus from a patient. The present concept exploits similar principles, but has various advantages in that a relatively greater suction power for a given volumetric flow rate than in conventional designs is believed to result from the unique geometric properties of catheter 10 and the other embodiments contemplated herein. These capabilities are expected to enable relatively smaller size catheters, or reduced flow rates, without sacrificing suction power. Analogously, substantially lowered fluid pressure and thus increased suction may be attained for a given size of catheter, potentially making treatment more rapid and/or improving the capability of treating mature, fibrous thrombi. Increased flow velocity of the fluid as compared with open, in other words non-channelized, rheolytic thrombectomy catheters is at least partly responsible for such improvements.

As noted above, inlet 32 may be one of a plurality of inlets, which may be elongate and spaced circumferentially about longitudinal axis 14 and each in fluid communication with second lumen 28. In a practical implementation strategy, at least one inlet 32 is spaced an axial distance 53 from at least one outlet 30, and channel 52 defines a flow path for a conveyed fluid having a path length greater than axial distance 53. Channel 52 may further have a helical shape, and advance at least one full turn about longitudinal axis 14, imparting analogous features to the fluid flow path. In the illustrated embodiment, flow directing mechanism 50 includes a vane 54 radially projecting from outer surface 20, with vane 54 forming a first sidewall 56 of channel 52 and a second sidewall 58 of channel 52. Vane 54 may further include a radially outward helical edge 60 formed by an intersection of sidewalls 56 and 58. Referring also now to FIG. 5, illustrating a perspective partial view of catheter 10, it may be noted that vane 54 advances in a helical path about catheter body 12. In one practical implementation strategy, vane 54 may have a constant pitch helical path, but in other embodiments the pitch of vane 54 might vary, for example beginning at a relatively steeper pitch close to outlet 30 and transitioning to a relatively shallower pitch towards inlet 32, or the reverse, to impart certain flow properties to fluid conveyed via channel 52. It may also be noted that vane 54, and in particular edge 60, is positioned at a more or less constant location radially outward from outer surface 20, but tapers inwardly to smoothly intersect with outer surface 20 at proximal and distal ends of vane 54.

It can be expected that flow directing mechanism 50 will affect flow of fluid pumped from outlet 30 to inlet 32 where the pumped fluid is traveling between opposed sidewalls 56 and 58, but can also affect flow where the pumped fluid first flows along only one of sidewalls 56 and 58 and last flows along only the other of sidewalls 56 and 58 as it travels between outlet 30 and inlet 32. Channel 52 can be understood to have an end or inlet opening where sidewalls 56 and 58 are first positioned in opposition to one another just distal to outlet 30, and another end or outlet opening/exit where sidewalls 56 and 58 cease to be in opposition to one another just proximal to inlet 32. Fluid flowing between outlet 30 and inlet 32 will thus be directed within channel 52, but can also be directed via impingement upon sidewalls 56 or 58 at locations where the pumped fluid is no longer considered to be conveyed within channel 52. As noted above, at least some fluid having exited channel 52 enters a suction stream flowing to inlet 32. Some of the fluid having been conveyed through channel 52 may continue a generally helical flow path about catheter 10 and enter another inlet 32 after having traveled one quarter, one half, or even one full additional turn about axis 14 after having exited channel 52. In still further instances, one or more outlets 32 might be positioned at least partially within channel 52 such that some fluid pumped between outlet 30 and inlet 32 never actually exits channel 52. Additional properties of the expected fluid flow during implementation of thrombectomy catheter 10 in a patient and associated methodology will be further apparent from the following description.

Referring now to FIG. 2, there is shown a catheter 110 according to another embodiment, and also including an elongate catheter body 112 having one or more outlets 130 and one or more inlets 132, and a flow directing mechanism 150 extending between outlet 130 and inlet 132. It may be noted from the FIG. 2 illustration that outlets and inlets 130 and 132 are elongate, and each has a major axis, one of which is shown via reference numeral 133 for one of inlets 132, which is substantially in alignment with a helical shape of flow directing mechanism 150, and a channel to be formed thereby as further discussed herein. Each of outlets 130 and inlets 132 will further be understood to define a minor axis, which would be oriented orthogonally to major axis 133. Another way to understand this feature is that a long dimension of at least inlets 132 and potentially outlets 130 will be substantially parallel to, or at least within about 45° of being parallel to, a helix defined by the channel formed by flow directing mechanism 150. Outlets and inlets in any of the other embodiments herein could be similarly configured. In FIG. 2, flow directing mechanism 150 is shown in a low profile configuration, but is adjustable to an expanded profile, deployed configuration. At the state depicted in FIG. 2, catheter 110 is shown as it might appear where first being placed within a body lumen such as a vein or artery in a patient.

Referring now to FIG. 3, there is shown catheter 110 as it might appear having been adjusted to an expanded profile, deployed configuration. In the illustrated embodiment, flow directing mechanism 150 includes a deformable wall 162 defining a cavity 164 formed between deformable wall 162 and elongate catheter body 112. Deformable wall 162 may include a conventional medical device balloon material attached to material of elongate catheter body 112. Elongate catheter body 112 defines a longitudinally extending control lumen 166 in fluid communication with cavity 164 for supplying an inflation fluid such as saline thereto. It can therefore be seen that catheter 110 can be adjusted from the low profile configuration as in FIG. 2 to the expanded profile deployed configuration as in FIG. 3 via supplying inflation fluid into cavity 164 to inflate mechanism 150, deforming wall 162 in a radially outward direction, and thereby form channel 152. Channel 152 may have features generally similar to those of channel 52 described in connection with catheter 10, and thus impart generally analogous flow properties to fluid pumped from outlets 130 to inlets 132. In FIG. 3, a longitudinally extending lumen 128 is shown connecting with inlets 132, which are shown in phantom. It will be appreciated that another lumen not visible in the section plane of FIG. 3 will connect with outlets 130, again in a way generally analogous to catheter 10 described in connection with FIGS. 1 and 5. When it is desirable to remove catheter 110 from a patient after thrombectomy, inflation fluid may be withdrawn from cavity 164 via control lumen 166, and mechanism 150 will deflate. Catheter 110 can then be withdrawn, potentially within a protective sheath as described in connection with other embodiments herein.

Referring now to FIG. 4, there is shown a catheter 210 according to another embodiment, and also including an elongate catheter body 212 having formed therein one or more outlets 230 and one or more inlets 232. Catheter 210 includes a flow directing mechanism 250 having a deployed configuration similar to that of catheters 10 and 110, and also a low profile configuration. Catheter body 212 will also be understood to define first and second longitudinally extending lumens fluidly connecting with outlets 230 and inlets 232, respectively, to enable fluid to be pumped therebetween. In catheter 210, flow directing mechanism 250 defines a channel 252 in an expanded profile, deployed configuration. Catheter 210 is shown as it might appear where a sheath 270 is being withdrawn from about flow directing mechanism 250. Mechanism 250 may include a deformable wall 254 attached to catheter body 212, and a spring frame 268 positioned between wall 254 and catheter body 212 and biasing wall 254 radially outward via a shape memory bias of spring frame 268. Sheath 270 may thus apply a condensing bias opposing the shape memory bias such that placing sheath 270 over mechanism 250 adjusts mechanism 250 in opposition to its shape memory bias from the expanded profile configuration forming channel 252 to the low profile configuration, and withdrawing sheath 270 does the reverse. Spring frame 268 might include metallic struts unattached, or attached to one another, and formed of nitinol, stainless steel, or any other suitable shape memory metallic material. Spring frame 268 might also be braided, woven, or of still another configuration. Deformable wall 254 may thus constitute a relatively thin layer of non-metallic, likely elastomeric material, that is shaped at least predominately via the shape memory bias of spring frame 268, at least where no external force opposing the shape memory bias is being applied. Spring frame 268 is shown positioned within a cavity 264 formed between deformable wall 254 and catheter body 212, but in alternative embodiments spring frame 268 might be formed integrally with or attached to material of deformable wall 254. In any event, withdrawing sheath 270 can enable mechanism 250 to spring outwardly into its deployed, configuration for use within a body lumen in a patient much in the manner described in connection with the foregoing embodiments. When it is desirable to withdraw catheter 210 from a patient, sheath 270 may be advanced back over mechanism 250 to collapse the same. It should be appreciated that the embodiment of FIGS. 1 and 5, catheter 10, might be delivered and withdrawn in a similar manner, and rather than utilizing a spring frame shape memory polymers or the like could be used to form vane 54.

INDUSTRIAL APPLICABILITY

Referring now to the drawings generally, but in particular to FIG. 6, there is shown a system 400 for treating thrombus in a patient, and including a pump 402 connected with catheter 10 in a conventional manner to supply a fluid such as saline, contrast, mixtures or still another fluid to catheter 10, and withdraw the same along with disrupted material 309 of a thrombus 308 within a body lumen 307 of a vessel 306 within a patient. It should be appreciated that pump 402 might pump the fluid into catheter 10, and withdraw fluid from catheter 10 to be discarded. The same fluid might be recirculated, however, with filtering mechanisms used to remove any materials which it is undesirable to reinject into the patient. Accordingly, no particular pumping strategy, filtering strategy, number of pumps, or any other limitation to pump 402 is intended by way of the present description.

Catheter 10 extends through a conventional introducer 300 passed percutaneously into body lumen 307 in a conventional manner. Catheter 10 also passes through a sheath 70 which can be used in a manner similar to that described above to constrain mechanism 50 for initial placement within body lumen 307, and then withdrawn to enable deployment of catheter 10. In the illustrated embodiment, catheter 10 is shown within body lumen 307 such that vane touches or nearly touches an inside diameter of vessel 306. The present concepts may be implemented in cases where there is very little or zero clearance between vane 54 and the inside diameter of a vessel, but may and typically will be implemented where there is some clearance such that the subject body lumen is unobstructed to fluid flow for at least some distance peripherally outward of vane 54.

Catheter 10 is depicted in FIG. 6 as it might appear where fluid is being pumped from outlet 30 to inlet 32. A series of curved flow arrows 311 illustrate an approximate direction of fluid flow from outlet 30 to inlet 32, and it can be noted that the fluid is flowing generally in a helical path about catheter 10, as directed and conveyed by channel 52. At least a portion of pumped fluid will be conveyed in this general manner, and pumped fluid may also be conveyed through any clearance that extends between vane 54 and the inside diameter of vessel 306. Consistent with the geometry of mechanism 50 in the illustrated embodiment, the pumped fluid or portion thereof may be conveyed through at least one full turn about the longitudinal axis of catheter 10. Prior to commencing pumping the fluid, flow directing mechanism 50 will have been deployed within body lumen 307 via withdrawing sheath 70. Deploying of various thrombectomy catheters contemplated herein may include deforming a wall of its flow directing mechanism in a radially outward direction so as to form the channel. Where the embodiment of FIG. 4 is used, spring frame 268 may prop the deformable wall 254 outwardly. In the case of the embodiment of FIGS. 2 and 3, flow directing mechanism 150 may be inflated and thus pressurized via the supplying of inflation fluid to cavity 164. In each of the illustrated embodiments, conveyance of the pumped fluid between the outlet and inlet could be understood as occurring via a helical vane of the corresponding flow directing mechanism, regardless of the particular structure forming the vane. In other embodiments, however, something other than a vane might be used.

Additional flow arrows 313 are shown in FIG. 6 and illustrate generally a flow path of fluid entraining disrupted material of thrombus 308 and flowing in a suction stream to inlet 32. The fluid pumped to inlet 32 will tend to have a lowered pressure, at least as it approaches inlet 32, in a well known manner, and thus can be understood to both form and enter a suction stream of lowered pressure fluid flowing to and entering inlet 32. It can be noted that a zone of lowered pressure is somewhat biased towards a distal tip of catheter 10. It is believed that the geometry of catheter 10, and in particular mechanism 50, serves to focus the low pressure zone generally in a distal direction from mechanism 50. While known thrombectomy catheters may certainly have a low pressure zone at a distal end of the catheter, mechanism 50 and the related mechanisms in other embodiments contemplated herein, is believed to focus the lowered pressure to enable advantageous use of the catheter in comparison with certain known designs. When thrombus 308 has been cleared to the satisfaction of the clinician, which may be determined with the assistance of radiography, sheath 70 may be advanced over mechanism 50 to deform mechanism 50 in opposition to its shape memory bias, typically elastic deformation, and the assembly of sheath 70 and catheter 10 can be withdrawn from the patient.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A thrombectomy catheter comprising:
an elongate catheter body defining a longitudinal axis extending between a proximal body end and a distal body end, and including an outer surface, and inner surfaces defining a longitudinally extending first lumen and a longitudinally extending second lumen;
the first lumen being fluidly connected with an outlet formed in the outer surface and located in the distal body end, and the second lumen being fluidly connected with an inlet formed in the outer surface and located in the distal body end for receiving fluid pumped from the outlet to the inlet for suction disruption of a thrombus;
a flow directing mechanism upon the distal body end forming a channel for conveying a portion of the fluid, the channel axially and circumferentially advancing about the elongate catheter body, and being positioned between the outlet and the inlet such that fluid having exited the channel enters a suction stream flowing to the inlet and entraining material of the disrupted thrombus;
wherein the flow directing mechanism is biased away from a low profile configuration toward an expanded deployed configuration; and
wherein the flow directing mechanism includes a deformable wall attached to the elongate catheter body, and spring frame that includes a plurality of metallic struts positioned between the deformable wall and the elongate catheter body and biasing the deformable wall radially outward via the shape memory bias of the metallic struts.

2. The catheter of claim 1 wherein the inlet is spaced an axial distance from the outlet, and the channel defines a flow path for the conveyed fluid having a path length greater than the axial distance.

3. The catheter of claim 2 wherein the channel has a helical shape and advances at least one full turn about the longitudinal axis.

4. The catheter of claim 3 wherein the inlet is one of a plurality of elongate inlets spaced circumferentially about the longitudinal axis and each in fluid communication with the second lumen.

5. The catheter of claim 3 wherein the flow directing mechanism includes a vane radially projecting from the outer surface.

6. The catheter of claim 5 wherein the vane forms sidewalls of the channel, and includes a radially outward helical edge formed by an intersection of the sidewalls.

7. The catheter of claim 3 wherein the flow directing mechanism has a shape memory bias, and is adjustable in opposition to the shape memory bias from the expanded, deployed configuration forming the channel to the low profile configuration.

8. A method of treating thrombus in a patient comprising the steps of:

biasing a flow directing mechanism of a thrombectomy catheter from a low profile configuration toward an expanded deployed configuration;
deploying the flow directing mechanism from the low profile configuration to the expanded deployed configuration responsive to moving flow directing mechanism from a position within a sheath to a position outside the sheath;
pumping fluid between an outlet and an inlet in the thrombectomy catheter defining a longitudinal axis and positioned within a body lumen in a patient;
disrupting a thrombus within the body lumen via suction induced by a lowered pressure of the pumped fluid flowing between the outlet and the inlet; and
conveying a portion of the pumped fluid through an axially and circumferentially advancing channel formed by the flow directing mechanism of the thrombectomy catheter between the outlet and the inlet, such that fluid having exited the channel enters a suction stream flowing to the inlet and entraining material of the disrupted thrombus;
wherein the step of deploying further includes deforming a wall of the flow directing mechanism in a radially outward direction so as to form the channel; and
wherein deforming the wall includes propping the wall radially outwardly via a spring frame dun includes a plurality of metallic struts positioned between an elongate body of the thrombectomy catheter and the wall.

9. The method of claim 8 wherein the step of conveying includes conveying the fluid through at least one full turn about the longitudinal axis.

10. The method of claim 9 wherein the deploying step is performed prior to commencing the step of pumping.

11. The method of claim 10, wherein the step of conveying includes conveying the fluid via a helical vane of the flow directing mechanism.

12. The method of claim 11 wherein the step of deploying further includes deploying the flow directing mechanism via withdrawing a sheath holding the helical vane in an elastically deformed, low profile configuration.

13. A thrombectomy catheter/sheath assembly comprising:
a sheath;
an elongate catheter body slidably positioned in the sheath and defining a longitudinal axis extending between a proximal body end and a distal body end, and including an outer surface, and inner surfaces defining a longitudinally extending first lumen and a longitudinally extending second lumen;
the first lumen being fluidly connected with an outlet formed in the outer surface and located in the distal body end, and the second lumen being fluidly connected with an inlet formed in the outer surface and located in the distal body end for receiving fluid pumped from the outlet to the inlet for suction disruption of a thrombus,
a flow directing mechanism upon the distal body end forming a channel for conveying a portion of the fluid, the channel axially and circumferentially advancing about the elongate catheter body and being positioned between the outlet and the inlet such that fluid having exited the channel enters a suction stream flowing to the inlet and entraining material of the disrupted thrombus;
wherein the flow directing mechanism is biased away from a low profile configuration toward an expanded deployed configuration, and the flow directing mechanism changes from the low profile configuration to the expanded deployed configuration responsive to moving the flow directing mechanism from a position within the sheath to a position outside the sheath; and
wherein the flow directing mechanism includes a spring frame comprising a plurality of metallic struts.

\* \* \* \* \*